US010072078B2

(12) United States Patent
Orentas et al.

(10) Patent No.: US 10,072,078 B2
(45) Date of Patent: Sep. 11, 2018

(54) M971 CHIMERIC ANTIGEN RECEPTORS

(71) Applicant: The United States of America, as represented by the Secretary, Department of Health and Human Services, Washington, DC (US)

(72) Inventors: Rimas J. Orentas, Washington, DC (US); Ira H. Pastan, Potomac, MD (US); Dimiter S. Dimitrov, Frederick, MD (US); Crystal L. Mackall, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/437,889

(22) PCT Filed: Sep. 18, 2013

(86) PCT No.: PCT/US2013/060332
§ 371 (c)(1),
(2) Date: Apr. 23, 2015

(87) PCT Pub. No.: WO2014/065961
PCT Pub. Date: May 1, 2014

(65) Prior Publication Data
US 2015/0299317 A1 Oct. 22, 2015

Related U.S. Application Data

(60) Provisional application No. 61/717,960, filed on Oct. 24, 2012.

(51) Int. Cl.
*C07K 16/28* (2006.01)
*C07K 16/30* (2006.01)
*C07K 16/46* (2006.01)
*A61K 39/00* (2006.01)
*C12N 5/0783* (2010.01)

(52) U.S. Cl.
CPC ...... *C07K 16/2803* (2013.01); *A61K 39/0011* (2013.01); *C07K 16/3061* (2013.01); *C12N 5/0638* (2013.01); *A61K 2039/5156* (2013.01); *A61K 2039/5158* (2013.01); *C07K 2319/03* (2013.01); *C07K 2319/74* (2013.01); *C12N 2501/505* (2013.01); *C12N 2501/599* (2013.01); *C12N 2510/00* (2013.01)

(58) Field of Classification Search
None
See application file for complete search history.

(56) References Cited

U.S. PATENT DOCUMENTS

| 3,832,253 A | 8/1974 | Di Palma et al. |
|---|---|---|
| 3,854,480 A | 12/1974 | Zaffaroni |
| 4,235,871 A | 11/1980 | Papahadjopoulos et al. |
| 4,450,150 A | 5/1984 | Sidman |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | de Rham |
| 4,837,028 A | 6/1989 | Allen |
| 5,019,369 A | 5/1991 | Presant et al. |
| 5,075,109 A | 12/1991 | Tice et al. |
| 5,087,616 A | 2/1992 | Myers et al. |
| 5,225,539 A | 7/1993 | Winter |
| 5,239,660 A | 8/1993 | Ooi |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 6,265,150 B1 | 7/2001 | Terstappen et al. |
| 2002/0197266 A1 | 12/2002 | Debinski |
| 2003/0235869 A1 | 12/2003 | Popplewell et al. |
| 2010/0105136 A1 | 4/2010 | Carter et al. |
| 2011/0020344 A1 | 1/2011 | Dimitrov et al. |
| 2014/0274909 A1* | 9/2014 | Orentas ............ C07K 16/2803 514/19.3 |

FOREIGN PATENT DOCUMENTS

| EP | 0 239 400 B1 | 8/1994 |
|---|---|---|
| GB | 2 188 638 A | 10/1987 |

(Continued)

OTHER PUBLICATIONS

Imai et al., Leukemia, 2004, 18:676-684.*
Bang et al., "HA22 (R490A) is a recombinant immunotoxin with increased antitumor activity without an increase in animal toxicity," *Clin. Cancer Res.*, 11 (4), 1545-1550 (2005).
Capecchi, "High efficiency transformation by direct microinjection of DNA into cultured mammalian cells," *Cell*, 22 (2 Pt 2), 479-488 (1980).
Cartellieri et al., "Chimeric Antigen Receptor-Engineered T Cells for Immunotheraphy of Acute Myeloid Leukemia," *Blood*, 118 (21) Abstract 2618, 1124-1125 (2011).
Chu et al., "SV40 DNA transfection of cells in suspension: analysis of efficiency of transcription and translation of T-antigen," *Gene*, 13 (2), 197-202 (1981).

(Continued)

*Primary Examiner* — Hong Sang
(74) *Attorney, Agent, or Firm* — Leydig, Voit & Mayer, LTD.

(57) ABSTRACT

The invention provides a chimeric antigen receptor (CAR) comprising an antigen binding domain comprising SEQ ID NOs: 1-6, a transmembrane domain, and an intracellular T cell signaling domain. Nucleic acids, recombinant expression vectors, host cells, populations of cells, antibodies, or antigen binding portions thereof, and pharmaceutical compositions relating to the CARs are disclosed. Methods of detecting the presence of cancer in a mammal and methods of treating or preventing cancer in a mammal are also disclosed.

Figure 1:
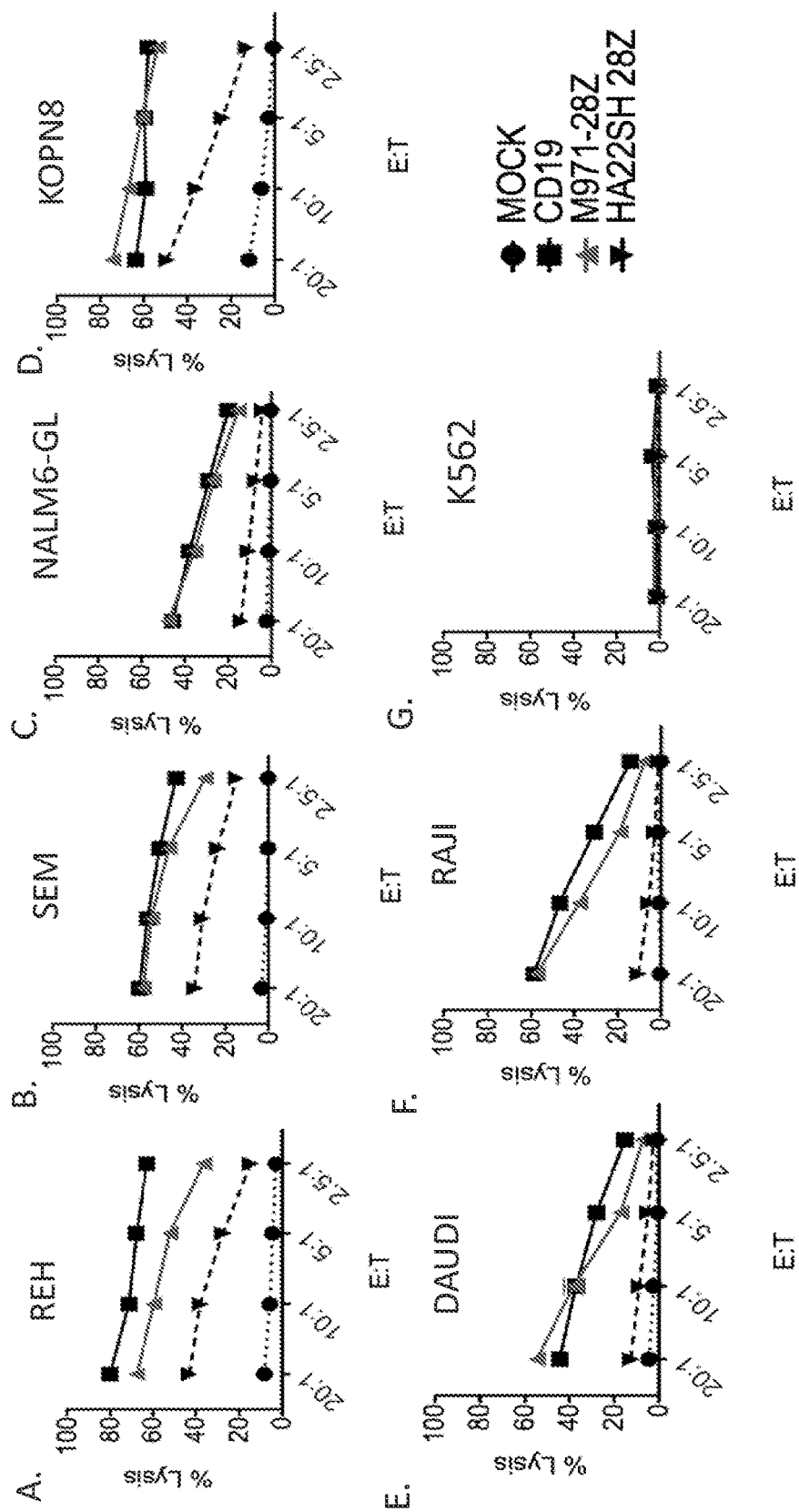

18 Claims, 6 Drawing Sheets
Specification includes a Sequence Listing.

(56) References Cited

FOREIGN PATENT DOCUMENTS

| RU | 2342401 C2 | 12/2008 |
|---|---|---|
| WO | WO 2009/091826 A2 | 7/2009 |
| WO | WO 2009/124109 A1 | 10/2009 |
| WO | WO 2011/041093 A1 | 4/2011 |
| WO | WO 2012/079000 A1 | 6/2012 |
| WO | WO 2013/059593 A1 | 4/2013 |

OTHER PUBLICATIONS

Clay et al., "Efficient transfer of a tumor antigen-reactive TCR to human peripheral blood lymphocytes confers anti-tumor reactivity," *J. Immunol.*, 163 (1), 507-513 (1999).
Davies et al., "Adoptive T-cell immunotherapy of cancer using chimeric antigen receptor-grafted T cells," *Arch. Immunol. Ther. Exp. (Warsz)*, 58 (3), 165-178 (2010).
Felgner et al., "Lipofection: a highly efficient, lipid-mediated DNA-transfection procedure," *Proc. Natl. Acad. Sci. USA*, 84 (21), 7413-7417 (1987).
Graham et al., "A new technique for the assay of infectivity of human adenovirus 5 DNA," *Virology*, 52 (2), 456-467 (1973).
Greenlee et al., "Cancer statistics, 2000," *CA Cancer J. Clin.*, 50 (1), 7-33 (2000).
Haskard et al., "The production of human monoclonal autoantibodies from patients with rheumatoid arthritis by the EBV-hybridoma technique," *J. Immunol. Methods.*, 74 (2), 361-367 (1984).
Haso et al., "Anti-CD22-chimeric antigen receptors targeting B-cell precursor acute lymphoblastic leukemia," *Blood*, 121 (7), 1165-1174 (2013).
Haso et al., "Anti-CD22-chimeric antigen receptors targeting B-cell precursor acute lymphoblastic leukemia," *Blood*, prepublished online Dec. 14, 2012.
Haso et al., "Targeting CD22 Expressing B Cell Leukemia with Chimeric Antigen Receptors (CAR): Engineering Membrane Proximity and Second Signaling Motifs for Optimal Activity," *J. Immunother.*, 35 (9), 723 (2012) abstract.
Haso et al., poster entitled "Enhancing Anti-CD22 Chimeric Antigen Receptor (CAR) Activity by Altering the Target Antigen Binding Site," presented at the 3rd International Conference on Immunotherapy in Pediatric Oncology, Frankfurt am Main, Oct. 1, 2012.
Hudecz, "Synthesis of Peptide Bioconjugates," *Methods Mol. Biol.*, 298, 209-223 (2005).
Huse et al., "Generation of a large combinatorial library of the immunoglobulin repertoire in phage lambda," *Science*, 246 (4935), 1275-1281 (1989).
International Preliminary Report on Patentability, Application No. PCT/US2013/060332, dated May 7, 2015.
International Search Report, Application No. PCT/US2013/060332, dated Nov. 14, 2013.
James et al., "Antigen sensitivity of CD22-specific chimeric TCR is modulated by target epitope distance from the cell membrane," *J. Immunol.*, 180 (10), 7028-7038 (2008).
Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).
Klein et al., "High-velocity microprojectiles for delivering nucleic acids into living cells," *Nature*, 327, 70-73 (1987).
Kochenderfer et al., "Eradication of B-lineage cells and regression of lymphoma in a patient treated with autologous T cells genetically engineered to recognize CD19," *Blood*, 116 (20), 4099-4102 (2010).
Köhler et al., "Derivation of specific antibody-producing tissue culture and tumor lines by cell fusion," *Eur. J. Immunol.*, 6, 511-519 (1976).
Long et al., Lessons learned from a highly-active CD22-specific chimeric antigen receptor, *Oncoimmunology*, 2 (4), e23621, 1-3 (2013).
Mannino et al., "Liposome mediated gene transfer," *BioTechniques*, 6 (7), 682-690 (1988).
Park et al., "Adoptive immunotherapy for B-cell malignancies with autologous chimeric antigen receptor modified tumor targeted T cells," *Discovery Med.*, 9 (47), 277-288 (2010).
Pedersen et al., "Comparison of surface accessible residues in human and murine immunoglobulin Fv domains. Implication for humanization of murine antibodies," *J. Mol. Biol.*, 235 (3), 959-973 (1994).
Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).
Roder et al., "The EBV-hybridoma technique," *Methods Enzymol.*, 121, 140-167 (1986).
Sadelain et al., "The promise and potential pitfalls of chimeric antigen receptors," *Curr. Opin. Immunol.*, 21 (2), 215-223 (2009).
Shigekawa et al., "Electroporation of eukaryotes and prokaryotes: a general approach to the introduction of macromolecules into cells," *Bio Techniques*, 6 (8), 742-751 (1988).
Szoka et al., "Comparative properties and methods of preparation of lipid vesicles (liposomes)," *Ann. Rev. Biophys. Bioeng.*, 9, 467-508 (1980).
Vaickus et al., "Immune markers in hematologic malignancies," *Crit. Rev. Oncol. Hematol.*, 11 (4), 267-297 (1991).
Wadwa et al., "Receptor mediated glycotargeting," *J. Drug Targeting*, 3 (2), 111-127 (1995).
Written Opinion of the International Searching Authority, Application No. PCT/US2013/060332, dated Nov. 14, 2013.
Xiao et al., "Identification and characterization of fully human anti-CD22 monoclonal antibodies," *Mabs*, 1 (3), 297-303 (2009).
Zhao et al., "A herceptin-based chimeric antigen receptor with modified signaling domains leads to enhanced survival of transduced T lymphocytes and antitumor activity," *J. Immunol.*, 183 (9), 5563-5574 (2009).
Zhao et al., "Primary human lymphocytes transduced with NY-ESO-1 antigen-specific TCR genes recognize and kill diverse human tumor cell lines," *J. Immunol.*, 174 (7), 4415-4423 (2005).
Frankel, et al., "Characterization of Diptheria Fusion Proteins Targeted to the Human Interleukin-3 Receptor," *Protein Engineering*, 13(8): 575-581 (2000).
Russian Patent Office, Office Action issued in counterpart Russian Patent Application No. 2015117237, dated Mar. 27, 2017, 9 pages.
Abate-Daga et al., "CAR models: Next Generation CAR Modifications for Enhanced T-cell function," *Molecular Therapy—Oncolytics* 3, 16014 (2016) 7 pages.
Baas, "Keys to the CAR," *SciBX: Science-Business eXchange*: 7(25) (2014) 7 pages.
Curran et al., "Chimeric Antigen Receptors for T Cell Immunotherapy: Current Understanding and Future Direction," *J Gene Med* 14(6): 405-415 (2012) (Author Manuscript).
Dotti et al., "Design and Development of Therapies Using Chimeric Antigen Receptor-Expressing T Cells," *Immunol. Rev.*, 257(1): 107-126 (2014) (Author Manuscript).
Grada et al., "TanCAR: A Novel Bispecific Chimeric Antigen Receptor for Cancer Immunotherapy," *Molecular Therapy—Nucleic Acids* 2, e105 (2013) 11 pages.
Holzinger et al., "CARs on the Highway: Chimeric Antigen Receptor Modified T Cells for the Adoptive Cell Therapy of Malignant Diseases," *Immunotherapy—Myths, Reality, Ideas, Future*, Metodiev ed., Chapter 9: 169-199 (2017).
Jain et al., "Overview of Recent Developments in Chronic Lymphocytic Leukemia," *South Asian J Cancer*, 1(2): 84-89 (2012).
Jensen et al., "Designing Chimeric Antigen Receptors to Effectively and Safely Target Tumors," *Curr Opin Immunol.*, 33: 9-15 (2015) (Author Manuscript).
Karpanen et al., "T-Cell Receptor Gene Therapy—ready to go Viral?" *Molecular Oncology*,9: 2019-2042 (2015).
Long et al., "4-1BB Costimulation Ameliorates T Cell Exhaustion Induced by Tonic Signaling of Chimeric Antigen Receptors," *Nature Medicine*, 21(6): 581-593 (2015).
National Cancer Institute, "CAR T Cells: Engineering Patients' Immune Cells to Treat their Cancers," (2017) 10 pages.
Newick et al., "Chimeric Antigen Receptor T-Cell Therapy for Solid Tumors," *Molecular Therapy—Oncolytics* 3, 16006 (2016) 7 pages.

(56) References Cited

OTHER PUBLICATIONS

Ramos et al., "Chimeric Antigen Receptor (CAR)—Engineered Lymphocytes for Cancer Therapy," *Expert Opin Biol Ther.*, 11(7): 855-873 (2011) (Author Manuscript).

Riddell et al., "Chimeric Antigen Receptor Modified T Cells—Clinical Translation in Stem Cell Transplantation and Beyond," *Biol Blood Marrow Transplant*; 19(1 0): S2-S5 (2013) (Author Manuscript).

Sadelain et al., "The Basic Principles of Chimeric Antigen Receptor (CAR) Design," *Cancer Discov*, 3(4): 388-398 (2013) (Author Manuscript).

Shirasu et al., "Functional Design of Chimeric T-Cell Antigen Receptors for Adoptive Immunotherapy of Cancer: Architecture and Outcomes," *Anticancer Research*, 32: 2377-2384 (2012).

Srivastava et al., "Engineering CAR-T Cells: Design Concepts," *Trends Immunol.*, 36(8): 494-502 (2015) (Author Manuscript).

Whilding et al., "CAR T-Cell Immunotherapy: The Path from the By-road to the Freeway," *Molecular Oncology*, 9: 1994-2018 (2015).

Wu et al., "Adoptive T-cell Therapy Using Autologous Tumor-infiltrating Lymphocytes for Metastatic Melanoma: Current Status and Future Outlook," *Cancer J*, 18(2): 160-175 (2012) (Author Manuscript).

Yu et al, "Chimeric Antigen Receptor T Cells: a Novel Therapy for Solid Tumors," *Journal of Hematology & Oncology* 10:78 (2017) 13 pages.

\* cited by examiner

M971 CHIMERIC ANTIGEN RECEPTORS

CROSS-REFERENCE TO RELATED APPLICATIONS

This application is a U.S. National Phase of International Patent Application No. PCT/US2013/060332, filed Sep. 18, 2013, which claims the benefit of U.S. Provisional Application No. 61/717,960, filed on Oct. 24, 2012, each of which is incorporated by reference in its entirety herein.

STATEMENT REGARDING FEDERALLY SPONSORED RESEARCH AND DEVELOPMENT

This invention was made with Government support under project number Z01 ZIA BC 010701 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 31,833 Byte ASCII (Text) file named "719873_ST25.txt," dated Apr. 22, 2015.

BACKGROUND OF THE INVENTION

Cancer is a public health concern. Despite advances in treatments such as chemotherapy, the prognosis for many cancers, including hematological malignancies, may be poor. For example, it has been estimated that more than 45,000 deaths were expected from non-Hodgkin's lymphoma and leukemia in the United States in 2000 (Greenlee et al., *CA Cancer J. Clin.*, 50:7-33 (2000)). Accordingly, there exists an unmet need for additional treatments for cancer, particularly hematological malignancies.

BRIEF SUMMARY OF THE INVENTION

An embodiment of the invention provides a chimeric antigen receptor (CAR) comprising an antigen binding domain comprising SEQ ID NOs: 1-6, a transmembrane domain, and an intracellular T cell signaling domain Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of cancer in a mammal and methods of treating or preventing cancer in a mammal.

BRIEF DESCRIPTION OF THE SEVERAL VIEWS OF THE DRAWING(S)

FIGS. 1A-1G are graphs showing % lysis of target $^{51}$Cr labeled leukemia cell lines REH (A), SEM (B), NALM6-GL (C), KOPN8 (D), Daudi (E), Raji (F), and K562 (G) by effector human T cells that were untransduced (mock, ●; circles) or transduced with the following CARs: HA22-SH-second generation, version 1 (▼), m971-second generation, version 1 (▲; open triangle), or CD19-specific CAR (■; squares) at various effector to target ratio (E:T) ratios.

Figure 2:
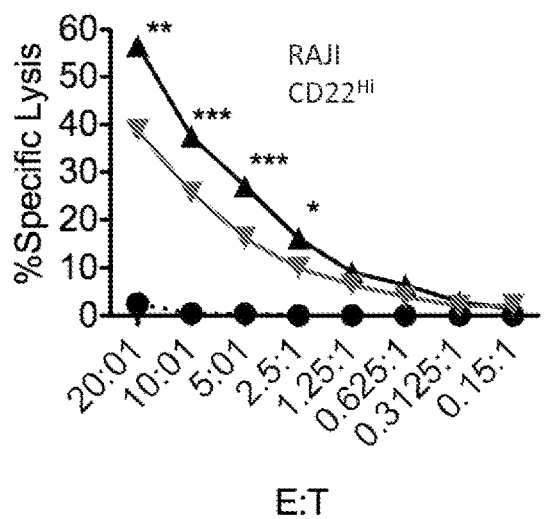
Figure 2:
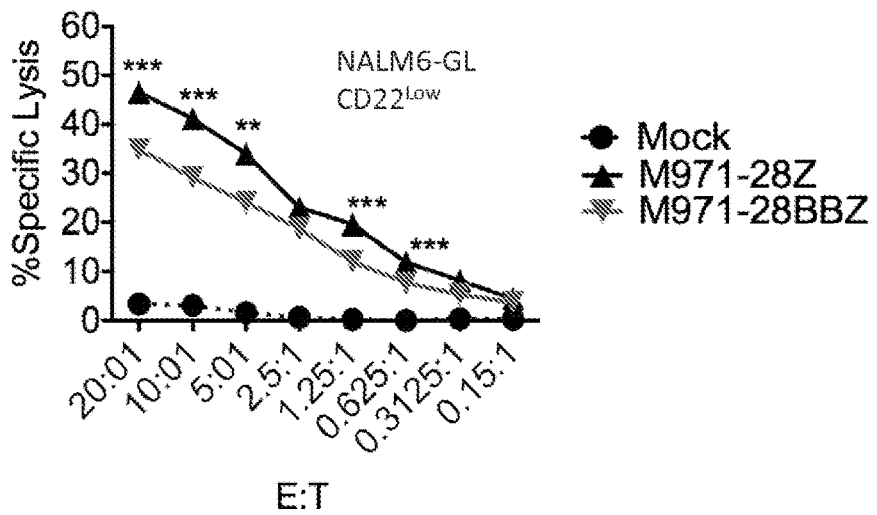
Figure 2:
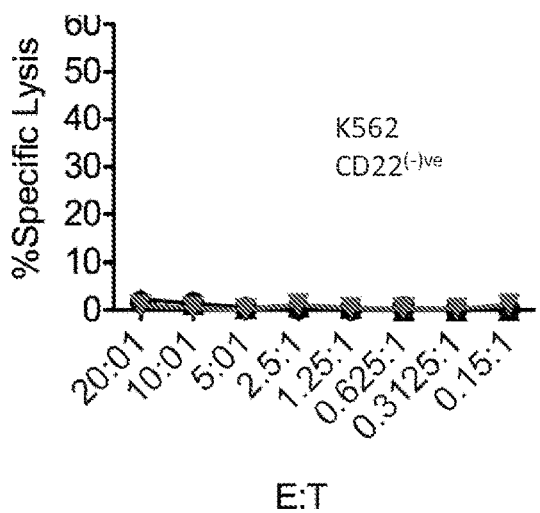

FIGS. 2A-2C are graphs showing percent lysis of target leukemia cell lines Raji (A), NALM6-GL (B), or K562 (C) by effector untransduced T cells (mock, ●; circles), m971-second generation, version 1 CAR (▲), or m971-third generation CAR (▼) at various E:T ratios.

Figure 3:
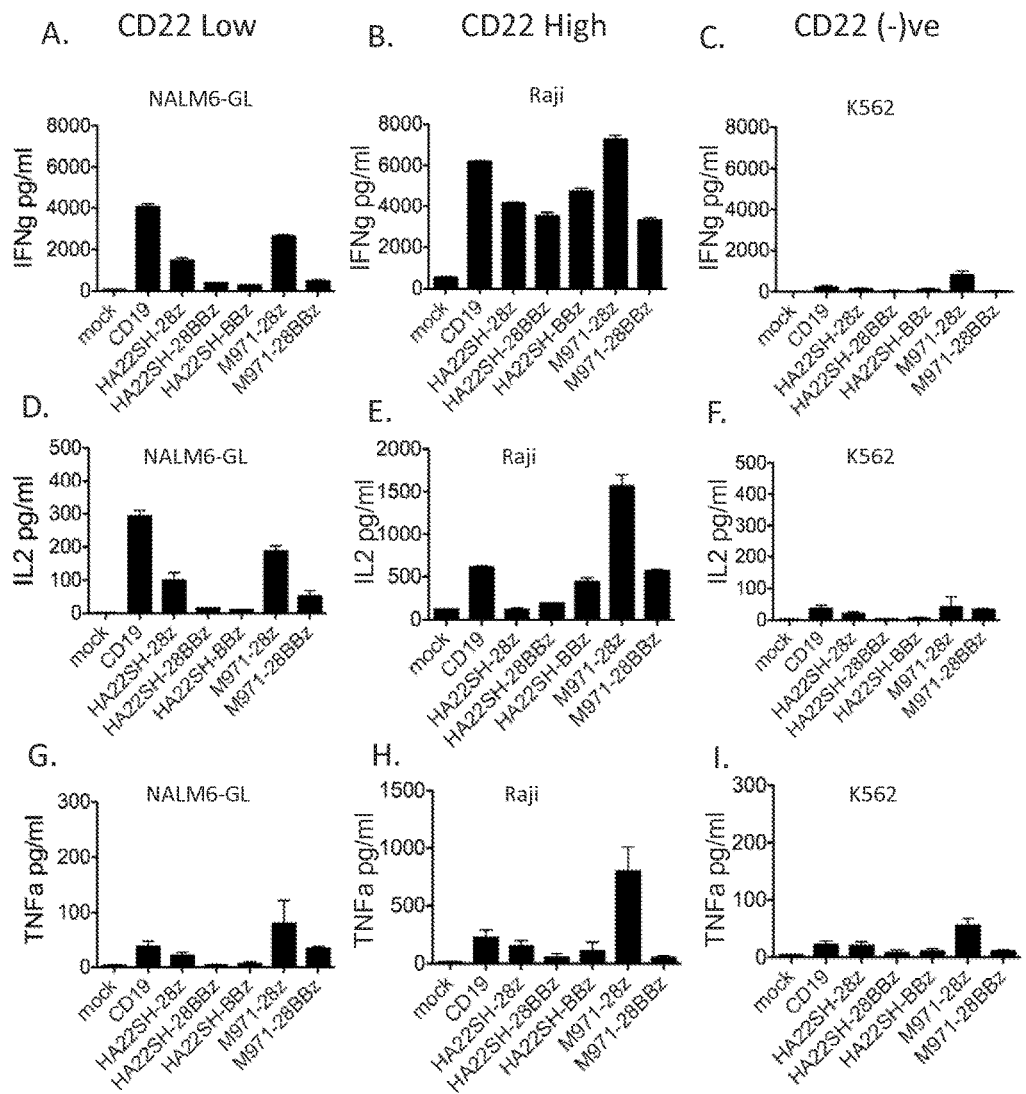

FIGS. 3A-3C are graphs showing the amounts of interferon (IFN)-γ (pg/ml) secreted by T cells that were untransduced (mock) or transduced with one of the following CARs: anti-CD19, m971-second generation version 1 (SEQ ID NO: 23), m971-third generation (SEQ ID NO: 24), HASH22-second generation version 1, HASH22-second generation version 2, or HASH22-third generation upon co-culture with leukemia cell lines NALM6-GL (CD22$^{low}$) (A), Raji (CD22$^{hi}$) (B), or K562 (CD22-negative) (C).

FIGS. 3D-3F are graphs showing the amounts of interleukin (IL)-2 (pg/ml) secreted by T cells that were untransduced (mock) or transduced with one of the following CARs: anti-CD19, m971-second generation version 1 (SEQ ID NO: 23), m971-third generation (SEQ ID NO: 24), HASH22-second generation version 1, HASH22-second generation version 2, or HASH22-third generation upon co-culture with leukemia cell lines NALM6-GL (CD22$^{low}$) (A), Raji (CD22$^{hi}$) (B), or K562 (CD22-negative) (C).

FIGS. 3G-3I are graphs showing the amounts of tumor necrosis factor (TNF)-α (pg/ml) secreted by T cells that were untransduced (mock) or transduced with one of the following CARs: anti-CD19, m971-second generation version 1 (SEQ ID NO: 23), m971-third generation (SEQ ID NO: 24), HASH22-second generation version 1, HASH22-second generation version 2, or HASH22-third generation upon co-culture with leukemia cell lines NALM6-GL (CD22$^{low}$) (A), Raji (CD22$^{hi}$) (B), or K562 (CD22-negative) (C).

Figure 4:
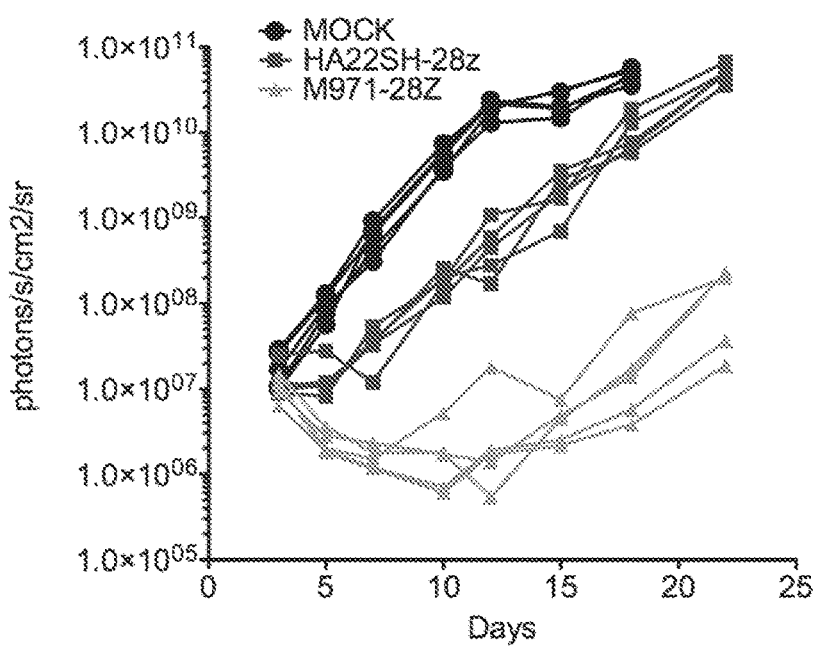
Figure 4:
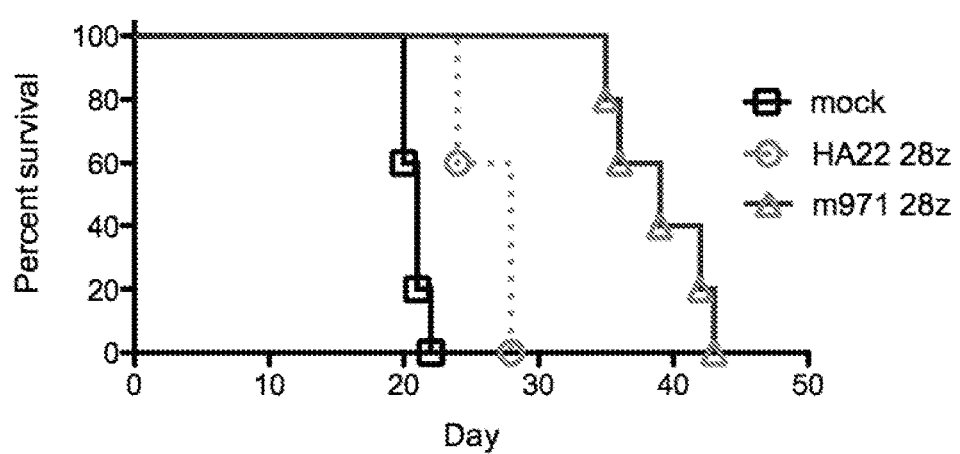

FIG. 4A is a graph showing bioluminescent signals (photons/s/cm$^2$/sr) generated by the reaction of luciferase (transfected into leukemia cells, which were injected into mice) with luciferin that was injected into the mice, measured over a time period of 30 days. The mice were treated with control T cells ("mock," untransduced, ●; circles) or T cells transduced with HASH22 CAR-second generation, version 1 (■; squares) or m971-second generation version 1 (triangles, SEQ ID NO: 23). Higher photons/s/cm$^2$/sr values indicates greater tumor burden.

FIG. 4B is a graph showing percent survival of mice treated with control T cells ("mock," untransduced, squares) or T cells transduced with HASH22 CAR-second generation version 1 (circles) or 971 CAR-second generation version 1 (triangles, SEQ ID NO: 23) over 30 days. (Mock v. HA22, p=0.0019; mock v. m971, p=0.0019; m971 v. HA22, p=0.003).

Figure 5:

FIG. 5 is a table showing bioluminescent images of mice having leukemia three, five, and eight days after treatment with untransduced T cells (mock) or 15×10$^6$, 5×10$^6$, 1×10$^6$, or 1×10$^5$ T cells that were transduced with a nucleotide sequence encoding a m971-second generation, version 2 CAR (SEQ ID NO: 22). A change in shading from grey to white indicates increased tumor burden.

Figure 6:
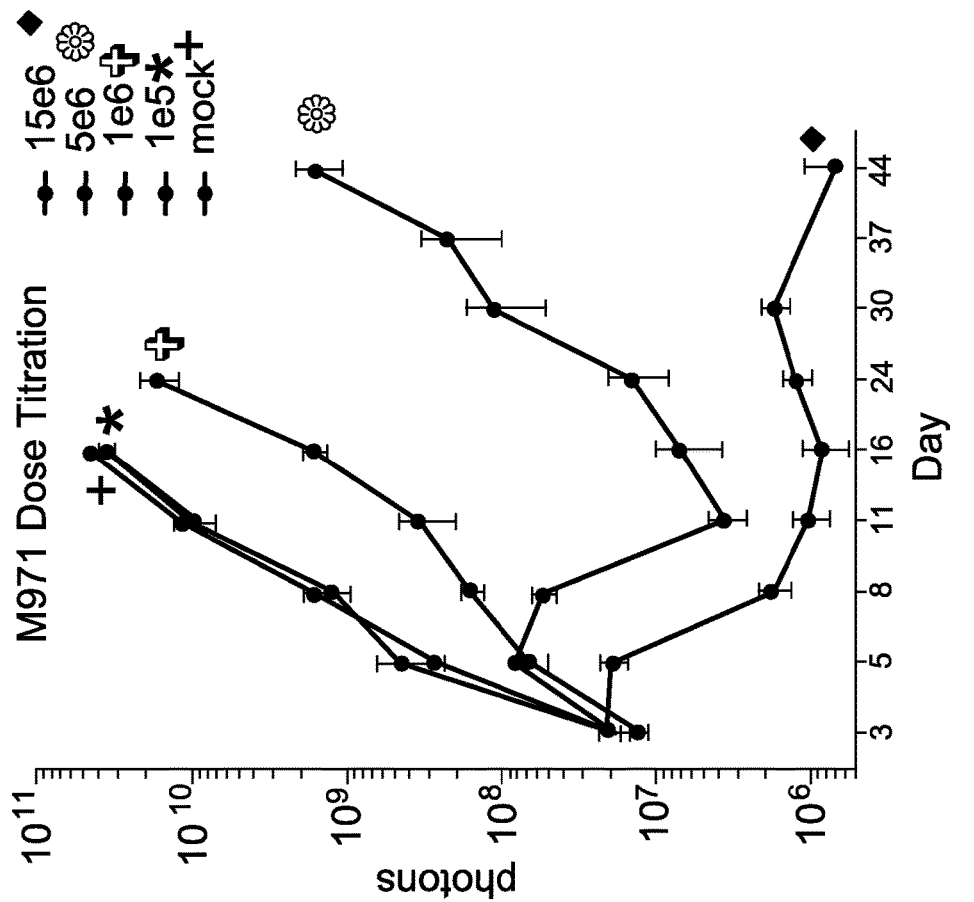

FIG. 6 is a graph showing the total number of photons emitted in the bioluminescence of the mice shown in FIG. 5 over a period of 44 days. The total number of photons was quantified and plotted, and the averages and standard deviations are shown for each time point. Mice were treated with untransduced T cells (mock) (plus sign) or 15×10$^6$ (diamond), 5×10$^6$ (flower), 1×10$^6$ (cross), or 1×10$^5$ (asterisk) T cells that were transduced with a nucleotide sequence encoding a m971-second generation, version 2 CAR (SEQ ID NO: 22).

DETAILED DESCRIPTION OF THE INVENTION

An embodiment of the invention provides a chimeric antigen receptor (CAR) comprising an antigen binding domain comprising SEQ ID NOs: 1-6, a transmembrane domain, and an intracellular T cell signaling domain.

A CAR is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for CD22. CD22 is a lineage-restricted B cell antigen belonging to the immunoglobulin (Ig) superfamily. CD22 is expressed in 60-70% of B cell lymphomas and leukemias (e.g., B-chronic lymphocytic leukemia, hairy cell leukemia, acute lymphocytic leukemia (ALL), and Burkitt's lymphoma) and is not present on the cell surface in early stages of B cell development or on stem cells. Vaickus et al., *Crit. Rev. Oncol./Hematol.*, 11:267-297 (1991); Bang et al., *Clin. Cancer Res.*, 11: 1545-50 (2005).

Without being bound to a particular theory or mechanism, it is believed that by eliciting an antigen-specific response against CD22, the inventive CARs provide for one or more of any of the following: targeting and destroying CD22-expressing cancer cells, reducing or eliminating cancer cells, facilitating infiltration of immune cells to tumor site(s), and enhancing/extending anti-cancer responses. Because CD22 is not expressed in early stages of B cell development or on stem cells, it is contemplated that the inventive CARs advantageously substantially avoid targeting/destroying stem cells and/or B cells in early development stages.

An embodiment of the invention provides a CAR comprising an antigen binding domain of the m971 antibody ("m971"). The antigen binding domain of m971 specifically binds to CD22. In this regard, a preferred embodiment of the invention provides CARs comprising an antigen-binding domain comprising, consisting of, or consisting essentially of, a single chain variable fragment (scFv) of the antigen binding domain of m971. The m971 antibody provides improved binding to CD22 as compared to the HA22 immunotoxin and also binds to a different CD22 epitope. Xiao et al., *mAbs* 1:3, 297-303 (2009).

The antigen binding domain may comprise a light chain variable region and/or a heavy chain variable region. In an embodiment of the invention, the heavy chain variable region comprises a CDR1 region, a CDR2 region, and a CDR3 region. In this regard, the antigen binding domain may comprise one or more of a heavy chain CDR1 region comprising SEQ ID NO: 1; a heavy chain CDR2 region comprising SEQ ID NO: 2; and a heavy chain CDR3 region comprising SEQ ID NO: 3. Preferably, the heavy chain comprises all of SEQ ID NOs: 1-3.

In an embodiment of the invention, the light chain variable region may comprise a light chain CDR1 region, a light chain CDR2 region, and a light chain CDR3 region. In this regard, the antigen binding domain may comprise one or more of a light chain CDR1 region comprising SEQ ID NO: 4; a light chain CDR2 region comprising SEQ ID NO: 5; and a light chain CDR3 region comprising, SEQ ID NO: 6. Preferably, the light chain comprises all of SEQ ID NOs: 4-6. In an especially preferred embodiment, the antigen binding domain comprises all of SEQ ID NO: 1-6.

The light chain variable region of the antigen binding domain may comprise, consist of, or consist essentially of, SEQ ID NO: 7. The heavy chain variable region of the antigen binding domain may comprise, consist of, or consist essentially of, SEQ ID NO: 8. Accordingly, in an embodiment of the invention, the antigen binding domain comprises a light chain variable region comprising SEQ ID NO: 7 and/or a heavy chain variable region comprising SEQ ID NO: 8. Preferably, the antigen binding domain comprises both SEQ ID NOs: 7 and 8.

In an embodiment of the invention, the light chain variable region and the heavy chain variable region may be joined by a linker. The linker may comprise any suitable amino acid sequence. In an embodiment of the invention, the linker may comprise, consist, or consist essentially of, SEQ ID NO: 11.

In an embodiment, the antigen binding domain comprises a light chain variable region and a heavy chain variable region. In this regard, an embodiment of the antigen binding domain comprising both a light chain variable region and a heavy chain variable region comprises, consists of, or consists essentially of, SEQ ID NO: 9.

In an embodiment, the antigen binding domain comprises a leader sequence. The leader sequence may be positioned at the amino terminus of the light chain variable region. The leader sequence may comprise any suitable leader sequence. In an embodiment, the leader sequence is a human granulocyte-macrophage colony-stimulating factor (GM-CSF) receptor sequence. In this regard, the antigen binding domain comprises a leader sequence comprising, consisting of, or consisting essentially of SEQ ID NO: 10. In an embodiment of the invention, while the leader sequence may facilitate expression of the CAR on the surface of the cell, the presence of the leader sequence in an expressed CAR is not necessary in order for the CAR to function. In an embodiment of the invention, upon expression of the CAR on the cell surface, the leader sequence may be cleaved off of the CAR. Accordingly, in an embodiment of the invention, the CAR lacks a leader sequence.

In an embodiment of the invention, the CAR comprises a transmembrane domain. In an embodiment of the invention, the transmembrane domain comprises i) CD8 and/or ii) CD28. In a preferred embodiment, the CD8 and CD28 are human. The CD8 or CD28 may comprise less than the whole CD8 or CD28, respectively. In this regard, the CAR comprises a CD8 transmembrane domain comprising, consisting of, or consisting essentially of SEQ ID NO: 12 or 18 and/or a CD28 transmembrane domain comprising, consisting of, or consisting essentially of SEQ ID NO: 15.

In an embodiment of the invention, the CAR comprises an intracellular T cell signaling domain comprising any one or more of i) CD28, ii) CD137, and/or iii) CD3 zeta (ζ). In a preferred embodiment, the CD28, CD137, and CD3 zeta are human. CD28 is a T cell marker important in T cell co-stimulation. CD137, also known as 4-1BB, transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). The CD28, CD137, or CD3 zeta may comprise less than the whole CD28, CD137, or CD3 zeta, respectively. In this regard, the intracellular T cell signaling domain comprises a CD28 amino acid sequence comprising, consisting of, or consisting essentially of, SEQ ID NO: 16 or 19, a CD137 amino acid sequence comprising, consisting of, or consisting essentially of, SEQ ID NO: 13 or 20, and/or a CD3 zeta amino acid sequence comprising, consisting of, or consisting essentially of, SEQ ID NO: 14, 17, or 21.

In an embodiment of the invention, the CAR comprises a transmembrane domain comprising CD28 and an intracellular T cell signaling domain comprising CD28 and CD3 zeta. In this regard, the CAR may comprise each of SEQ ID NOs: 15-17. Preferably, the CAR comprises a) each of SEQ ID NOs: 1-6 and 15-17; b) 7-8 and 15-17; c) 9 and 15-17; or d) 9-10 and 15-17.

In an embodiment of the invention, the CAR comprises a transmembrane domain comprising CD8 and an intracellular T cell signaling domain comprising CD28, CD137, and CD3 zeta. In this regard, the CAR may comprise each of SEQ ID NOs: 18-21. Preferably, the CAR comprises a) each of SEQ ID NOs: 1-6 and 18-21; b) 7-8 and 18-21; c) 9 and 18-21; or d) 9-10 and 18-21.

In an embodiment of the invention, the CAR comprises a transmembrane domain comprising CD8 and an intracellular T cell signaling domain comprising CD137 and CD3 zeta. In this regard, the CAR may comprise each of SEQ ID NOs: 12-14. Preferably, the CAR comprises a) each of SEQ ID NOs: 1-6 and 12-14; b) 7-8 and 12-14; c) 9 and 12-14; or d) 9-10 and 12-14.

Additional embodiments of the invention provide CARs comprising, consisting of, or consisting essentially of any of, the amino acid sequences set forth in Table 1.

TABLE 1

| SEQ ID NO: | Antigen Binding Domain | Transmembrane and Signaling Domains |
|---|---|---|
| SEQ ID NO: 22 (second generation, version 2) | m971 | CD8 transmembrane domain CD137 and CD3ζ, intracellular T cell signaling domains |
| SEQ ID NO: 23 (second generation, version 1) | m971 | CD28 transmembrane domain CD28 and CD3ζ intracellular T cell signaling domains |
| SEQ ID NO: 24 (third generation) | m971 | CD8 transmembrane domain CD28, CD137, and CD3ζ intracellular T cell signaling domains |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 90%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 BI, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which is a truncated Fab fragment including the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

An embodiment of the invention provides a nucleic acid comprising a nucleotide sequence encoding a leader sequence and an antigen binding domain (including a light chain variable region and a heavy chain variable region. In this regard, the nucleic acid may comprise, consist of, or consist essentially of, SEQ ID NO: 25.

The nucleic acids of the invention may comprise a nucleotide sequence encoding any of the transmembrane domains and/or intracellular T cell signaling domains described herein. An embodiment of the invention provides a nucleic acid comprising a nucleotide sequence encoding a transmembrane domain comprising CD28, an intracellular T cell signaling domain comprising CD28, and an intracellular T cell signaling domain comprising CD3ζ. In this regard, the nucleic acid may comprise, consist of, or consist essentially of, SEQ ID NO: 27. Another embodiment of the invention provides a nucleic acid comprising a nucleotide sequence encoding a transmembrane domain comprising CD8, an intracellular T cell signaling domain comprising CD28, an intracellular T cell signaling domain comprising CD137, and an intracellular T cell signaling domain comprising CD3ζ. In this regard, the nucleic acid may comprise, consist of, or consist essentially of, SEQ ID NO: 28. Still another embodiment of the invention provides a nucleic acid comprising a nucleotide sequence encoding a transmembrane domain comprising CD8, an intracellular T cell signaling domain comprising CD137, and an intracellular T cell signaling domain comprising CD3ζ. In this regard, the nucleic acid may comprise, consist of, or consist essentially of, SEQ ID NO: 26.

In an embodiment of the invention, the nucleic acid comprises a nucleotide sequence that encodes a leader sequence, an antigen binding domain (including a light chain variable region and a heavy chain variable region), a transmembrane domain comprising CD28, an intracellular T cell signaling domain comprising CD28, and an intracellular T cell signaling domain comprising CD3ζ. In this regard, the nucleic acid may comprise, consist of, or consist essentially of, both SEQ ID NOs: 25 and 27.

In an embodiment of the invention, the nucleic acid comprises a nucleotide sequence that encodes a leader sequence, an antigen binding domain (including a light chain variable region and a heavy chain variable region), a transmembrane domain comprising CD8, an intracellular T cell signaling domain comprising CD28, an intracellular T cell signaling domain comprising CD137, and an intracellular T cell signaling domain comprising CD3ζ. In this regard, the nucleic acid may comprise, consist of, or consist essentially of, both SEQ ID NOs: 25 and 28.

In an embodiment, the nucleic acid comprises a nucleotide sequence that encodes a leader sequence, an antigen binding domain (including a light chain variable region and a heavy chain variable region), a transmembrane domain comprising CD8, an intracellular T cell signaling domain comprising CD137, and an intracellular T cell signaling domain comprising CD3ζ. In this regard, the nucleic acid may comprise, consist of, or consist essentially of, both SEQ ID NOs: 25 and 26.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the CAR and which may or may not be translated upon expression of the nucleic acid by a host cell.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than nonspecific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. In some embodiments, the vector can be a transposon.

A number of transfection techniques are generally known in the art (see, e.g., Graham et al., *Virology*, 52: 456-467 (1973); Sambrook et al., supra; Davis et al., *Basic Methods in Molecular Biology*, Elsevier (1986); and Chu et al., *Gene*, 13: 97 (1981). Transfection methods include calcium phosphate co-precipitation (see, e.g., Graham et al., supra), direct micro injection into cultured cells (see, e.g., Capecchi, *Cell*, 22: 479-488 (1980)), electroporation (see, e.g., Shigekawa et al., *BioTechniques*, 6: 742-751 (1988)), liposome mediated gene transfer (see, e.g., Mannino et al., *Bio Techniques*, 6: 682-690 (1988)), lipid mediated transduction (see, e.g., Felgner et al., *Proc. Natl. Acad. Sci. USA*, 84: 7413-7417 (1987)), and nucleic acid delivery using high velocity microprojectiles (see, e.g., Klein et al., *Nature*, 327: 70-73 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. Examples of sequences including termination codons include SEQ ID NOs: 32-33. The recombinant expression vector may comprise restriction sites to facilitate cloning. Examples of sequences including restriction sites include SEQ ID NOs: 29-31.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermnnal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. When the inventive CAR material is a host cell, an exemplary dose of host cells may be a minimum of one million cells (1 mg cells/dose). When the inventive CAR material is a nucleic acid packaged in a virus, an exemplary dose of virus may be 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linker to a targeting moiety. The practice of conjugating compounds, e.g., inventive CAR materials, to targeting moieties is known in the art. See, for instance, Wadwa et al., J. Drug Targeting 3: 111 (1995) and U.S. Pat. No. 5,087,616.

Alternatively, the inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. For purposes of the inventive methods, wherein host cells or populations of cells are administered to the mammal, the cells can be cells that are allogeneic or autologous to the mammal.

It is contemplated that the inventive pharmaceutical compositions, CARs, nucleic acids, recombinant expression vectors, host cells, or populations of cells can be used in methods of treating or preventing a disease in a mammal. Without being bound to a particular theory or mechanism, the inventive CARs have biological activity, e.g., ability to recognize antigen, e.g., CD22, such that the CAR when expressed by a cell is able to mediate an immune response against the cell expressing the antigen, e.g., CD22, for which the CAR is specific. In this regard, an embodiment of the invention provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a hematological malignancy (e.g., leukemia or lymphoma, including but not limited to Hodgkin lymphoma, non-Hodgkin lymphoma, chronic lymphocytic leukemia, acute lymphocytic cancer, acute myeloid leukemia, B-chronic lymphocytic leukemia, hairy cell leukemia, acute lymphocytic leukemia (ALL), and Burkitt's lymphoma). Preferably, the cancer is characterized by the expression of CD22.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of the inventive CARs, nucleic acids, recombinant expression vectors, host cells, populations of cells, antibodies, or antigen binding portions thereof, or pharmaceutical compositions, for the treatment or prevention of cancer in a mammal.

Another embodiment of the invention provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytoxicity, as described in Zhao et al., *J. Immunol.*, 174: 4415-4423 (2005).

The following examples further illustrate the invention but, of course, should not be construed as in any way limiting its scope.

EXAMPLE 1

This example demonstrates the synthesis of anti-CD22 CARs, transduction of PBMC with anti-CD22 CARs, and analysis of CAR surface expression on transduced PBMC.

CAR-encoding sequences were synthesized using codon-optimization algorithms (Mr. Gene GmBH, Regensburg, Germany) and subcloned into "destination" vectors as described in (Zhao et al., *J. Immunol.*, 183(9):5563-74 (2009)) encoding a first version second generation CAR (CD28 transmembrane and intracellular T cell signaling domains and CD3-zeta chain intracellular T cell signaling domain), second version second generation CAR (CD8 transmembrane domain linked to CD137 and CD3-zeta T cell signaling domains), or a third generation CAR (CD8 transmembrane domain linked to CD28, CD137, and CD3-zeta intracellular T cell signaling domains) sequences as shown in Table A.

TABLE A

| SEQ ID NO: | Antigen Binding Domain | Further Components |
| --- | --- | --- |
| HA22CAR-second generation, version 1 | HA22 | CH2CH3<br>CD28 transmembrane domain<br>CD28 and CD3ζ intracellular T cell signaling domains |
| HA22 CAR-third generation | HA22 | CH2CH3<br>CD8 transmembrane domain<br>CD28, CD137, and CD3ζ intracellular T cell signaling domains |
| HASH22 CAR-second generation, version 1 | HA22 | short immunoglobulin constant domain sequence<br>CD28 transmembrane domain<br>CD28 and CD3ζ intracellular T cell signaling domains |
| HASH22 CAR-third generation | HA22 | short immunoglobulin constant domain sequence<br>CD8 transmembrane domain<br>CD28, CD137, and CD3ζ, intracellular T cell signaling domains |
| BL22 CAR-second generation | BL22 | CH2CH3<br>CD28 transmembrane domain<br>CD28 and CD3ζ intracellular T cell signaling domains |
| BL22 CAR-third generation | BL22 | CH2CH3<br>CD8 transmembrane domain<br>CD28, CD137, and CD3ζ intracellular T cell signaling domains |

TABLE A-continued

| SEQ ID NO: | Antigen Binding Domain | Further Components |
|---|---|---|
| HASH22 CAR-second generation, version 2 | HA22 | short immunoglobulin constant domain sequence<br>CD8 transmembrane domain<br>CD137 and CD3ζ intracellular T cell signaling domains |
| m971 CAR-second generation, version 1 (SEQ ID NO: 23) | m971 | CD28 transmembrane domain<br>CD28 and CD3ζ intracellular T cell signaling domains |
| m971 CAR-third generation (SEQ ID NO: 24) | m971 | CD8 transmembrane domain<br>CD28, CD137, and CD3ζ intracellular T cell signaling domains |
| m971 CAR-second generation, version 2 (SEQ ID NO: 22) | m971 | CD8 transmembrane domain<br>CD137 and CD3ζ intracellular T cell signaling domains |

Retroviral vector supernatants were created by transfecting 293GP cells with plasmids encoding CAR retroviral vectors and the RD114 envelope glycoprotein, collecting culture supernatants (s/n) 48-72 hours later. The culture supernatants were frozen or used immediately to transduce OKT3 and IL-2 activated human PBMC using the "on plate" method for 2 consecutive days (culture of lymphocytes on plates coated with RECTRONECTIN (Takara Bio Inc., Shiga, Japan) pre-exposed to dilutions of vector containing s/n) as previously described in Y. Zhao et al., *J. Immunol.*, 183: 5563 (2009). Also used in this study was retroviral s/n containing a CD19-specific CAR from a permanent producer cell line (Kochenderfer et al., *Blood*, 116: 4099 (2010)).

CAR expression on transduced T cells was determined by flow cytometry. To directly measure the number of cells able to bind CD22 by virtue of the CH2CH3 domain, goat anti-human IgG (H&L) (Invitrogen, Grand Island, N.Y.) was used. To detect non-CH2CH3 encoding CARs, CD22-Fc (R&D Systems) followed by anti IgG-Fc PE (Jackson ImmunoResearch, West Grove, Pa.). The HA22SH CAR expresses a short immunoglobulin constant domain sequence instead of CH2CH3. The CD19-CAR was detected using Protein L. Biotinylated protein L (50 ng/ul, Thermo Scientific, Waltham, Mass.) was bound, cells washed, then detected with SA-PE (4 ug/ml, BD Biosciences, Franklin Lakes, N.J.). For comparison, a CD19-CAR vector s/n was also evaluated. Flow cytometry experiments confirmed CAR expression on transduced T cells. Second generation CARs demonstrated increased surface expression levels as compared to third generation CARs as measured by mean fluorescence intensity (MFI).

EXAMPLE 2

This example demonstrates the expression of CD22 and CD19 antigens on leukemia cell lines.

Human leukemia cell lines (REH, SEM, NALM6, KOPN8, Daudi, Raji, and K562) were evaluated for the expression level of CD19 and CD22 on the cell surface using QUANTI-BRITE PE beads (BD Biosciences) and PE-labeled anti-CD19 and anti-CD22 antibody (Table 2). "Receptor Number Per Cell" indicates the approximate absolute number of molecules per cell on each of the indicated cell lines. Data were calculated by determining antibodies bound per cell (ABC) using the CELLQUEST software (BD) data analysis tools in accordance with the manufacturer's instructions.

TABLE 2

| Leukemia Cell Line | Receptor Number Per Cell |
|---|---|
| REH CD19 | 15,100 |
| SEM CD19 | 50,800 |
| NALM-6 CD19 | 50,500 |
| KOPN-8 CD19 | 60,800 |
| Daudi CD19 | 15,000 |
| Raji CD19 | 50,000 |
| K562 CD19 | <100 |
| REH CD22 | 7,000 |
| SEM CD22 | 7,000 |
| NALM-6 CD22 | 8,000 |
| KOPN-8 CD22 | 15,300 |
| Daudi CD22 | 8,000 |
| Raji CD22 | 60,800 |
| K562 CD22 | <200 |

EXAMPLE 3

This example demonstrates the lytic activity of cells expressing the second generation (version 1) m971 CAR.

To determine the lytic activity, leukemia cell lines (REH, SEM, NALM6, KOPN8, Daudi, Raji, and K562) were $^{51}$Cr labeled and used as targets in cytotoxicity assays. Cells were untransduced (mock) or were transduced with the second generation (version 1) m971 CAR (SEQ ID NO: 23), the anti-CD19 CAR, or the second generation (version 1) HASH22 CAR and were used as effector cells at various effector to target ratios in the cytotoxicity assays. Percent lysis of the target cells was measured and is shown in FIG. 1A-1G.

As shown in FIGS. 1A-1G, the cells transduced with the second generation (version 1) m971 CAR (SEQ ID NO: 23) lysed CD22-expressing leukemia cell lines REH, SEM, NALM6, KOPN8, Daudi, and Raji, and did not lyse non-CD22 expressing cell line K562. Cells transduced with the second generation (version 1) m971 CAR (SEQ ID NO: 23) demonstrated superior lytic ability as compared to cells transduced with the second generation (version 1) HASH22 CAR.

Seven BCP-ALL patient samples were analyzed for CD22 and CD19 expression. A wide range of antigen expression was seen, as demonstrated by flow cytometric analysis. Some patients showed strong positivity for both antigens while others had decreased CD22 staining. In each case, CD22-specific CARs conferred anti-leukemic lytic activity on third party lymphocytes.

EXAMPLE 4

This example demonstrates the lytic activity of T cells expressing an m971 CAR.

To determine if second or third generation CAR constructs provided increased lytic activity, leukemia cell lines Raji ($CD22^{hi}$), NALM6-GL ($CD22^{low}$), or K562 (CD22-negative) were $^{51}$Cr labeled and used as targets in cytotoxicity assays. Effector cells were human T cells that were untransduced (mock) or transduced with m971-second generation, version 1 CAR (SEQ ID NO: 23) or m971-third generation CAR (SEQ ID NO: 24). Effector cells were co-cultured with target cells at various effector to target (E:T) ratios. The results are shown in FIGS. 2A-2C.

As shown in FIGS. 2A-2C, second generation m971 CARs demonstrated superior lytic activity as compared to third generation m971 CARs.

EXAMPLE 5

This example demonstrates the reactivity of T cells expressing an m971 CAR.

T cells that were untransduced (mock) or transduced with one of the following CARs: anti-CD19, m971-second generation version 1 (SEQ ID NO: 23), m971-third generation (SEQ ID NO: 24), HASH22-second generation version 1, HASH22-second generation version 2, or HASH22-third generation were co-cultured with leukemia cell lines Raji ($CD22^{hi}$), NALM6-GL ($CD22^{low}$), or K562 (CD22-negative), and the amounts of interferon (IFN)-γ, tumor necrosis factor (TNF) α, and interleukin (IL)-2 secreted were measured. The results are shown in FIGS. 3A-3I.

As shown in FIGS. 3A-3I, cells transduced with m971-second generation, version 1 CAR secreted higher amounts of IFN-γ, IL-2, and TNFα in response to co-culture with CD22 expressing cell lines as compared to third generation m971 CARs.

EXAMPLE 6

This example demonstrates that cells transduced with the m971 CAR retards the progression of disease and lengthens the duration of survival in vivo as compared to an HA22 CAR.

NOD scid gamma, immune-deficient (NSG) mice were injected on day 0 with $0.5 \times 10^6$ NALM6-GL (NAML6 transfected with Luciferase). On Day 3, mice were treated with $1 \times 10^7$ untransduced (mock) T cells or T cells transduced with HASH22-second generation, version 1 CAR or m971-second generation, version 1 CAR (SEQ ID NO: 23). Tumor burden was measured in terms of bioluminescent signals per each mouse as photons/s/cm$^2$/sr with bioluminescent imaging using the Xenogen IVIS instrument. Mice were injected intraperitoneally (i.p.) with 3 mg D-luciferin (Caliper Life Sciences, Inc., Hopkinton, Mass.) and 4 minutes post-injection, anesthetized mice were imaged with an exposure time of 30 seconds. LIVING IMAGE software was used to analyze the bioluminescent signals per each mouse as photons/s/cm$^2$/sr on days 3, 7, and 15. Signal intensity was plotted over time, and the results are shown in FIG. 4A.

As shown in FIG. 4A, all mice had equivalent disease on Day 3. Mice treated with T cells transduced with m971-second generation, version 1 CAR (SEQ ID NO: 23) reduced the tumor burden in mice as compared to mice treated with control cells or cells transduced with HA22 CAR.

Survival of the mice was measured for 50 days, survival statistics were calculated using Log-rank (Mantel-Cox) analysis, and the survival results are shown in FIG. 4B. As shown in FIG. 4B, mice treated with T cells transduced with m971-second generation, version 1 CAR (SEQ ID NO: 23) demonstrated increased survival as compared to mice treated with control cells transduced with HA22 CAR.

To determine if treatment failure was due to antigenic loss, mice were euthanized due to disease burden according to institutional protocol, and spleens analyzed by flow cytometry. Prior to therapy, high levels of CAR expression were seen on HASH-28z and m971-28z transduced T cells, and the NALM6-GL cells expressed both CD19 and CD22. Upon sacrifice, spleens were analyzed first for human CD45 and GFP expression. Gated GFP positive cells represent tumor, and upon further analysis this gate population continued to express GFP. However, any CD45 positive and GFP negative cells remaining no longer expressed the anti-CD22 CAR. This indicates that the leukemia continued to express CD22 and that CAR T cells did not persist at the time of sacrifice. When the experiment was repeated and mice sacrificed on day 12, when therapeutic T cells were still having an effect, they could readily be detected in the blood, spleen, and bone marrow. The m971-28z (second generation, version 1) CAR showed a much greater ability to infiltrate the bone marrow.

EXAMPLE 7

This example demonstrates a dose response curve for the adoptive transfer of cells expressing an m971 CAR.

NSG (immunodeficient) mice were injected with $0.5 \times 10^6$ NALM6-GL cells on day 0. On day 3, the animals were imaged using luciferin substrate to confirm the presence of leukemia. On day 3, leukemia-bearing mice were injected intravenously (i.v.) with untransduced (mock) T cells or $15 \times 10^6$, $5 \times 10^6$, $1 \times 10^6$, or $1 \times 10^5$ T cells transduced with a nucleotide sequence encoding a m971-second generation, version 2 CAR (SEQ ID NO: 22). The CAR transduction efficiency of the transduced T-cells was 90%. T cells were stimulated with anti-CD3/CD28 beads (1:1), cultured in 40 units/ml interleukin-2, and injected into the mice 10 days after the initial stimulation. Mice were imaged again on day 5 and day 8. The results are shown in FIGS. 5 and 6. A change in shading from grey to white indicates increased tumor burden in FIG. 5. In FIG. 6, a decrease in photons indicates a decrease in tumor burden. As shown in FIGS. 5 and 6, complete elimination of the leukemia was seen with the highest dose level by day 8.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) comprising an antigen binding domain comprising the amino acid sequences of SEQ ID NOs: 1-6, a transmembrane domain, and an intracellular T cell signaling domain.

2. The CAR according to claim 1, wherein the antigen binding domain comprises a light chain variable region comprising an amino acid sequence comprising SEQ ID NO: 7.

3. The CAR according to claim 1, wherein the antigen binding domain comprises a heavy chain variable region comprising an amino acid sequence comprising SEQ ID NO: 8.

4. The CAR according to claim 1, wherein the antigen binding domain comprises an amino acid sequence comprising SEQ ID NO: 9.

5. The CAR according to claim 1, wherein the antigen binding domain comprises a linker comprising SEQ ID NO: 11.

6. The CAR according to claim 1, further comprising a leader sequence comprising SEQ ID NO: 10.

7. The CAR according to claim 1, wherein the transmembrane domain comprises i) a transmembrane portion of a CD8 and/or ii) a transmembrane portion of a CD28.

8. The CAR according to claim 1, wherein the transmembrane domain comprises an amino acid sequence comprising SEQ ID NO: 12 or 18 and/or an amino acid sequence comprising SEQ ID NO: 15.

9. The CAR according to claim 1, wherein the intracellular T cell signaling domain comprises one or more of i) an intracellular signaling portion of a CD28, ii) an intracellular signaling portion of a CD137, and iii) an intracellular signaling portion of a CD3 zeta.

10. The CAR according to claim 1, wherein the intracellular T cell signaling domain comprises an amino acid sequence comprising SEQ ID NO: 16 or 19.

11. The CAR according to claim 1, wherein the intracellular T cell signaling domain comprises an amino acid sequence comprising SEQ ID NO: 13 or 20.

12. The CAR according to claim 1, wherein the intracellular T cell signaling domain comprises an amino acid sequence comprising SEQ ID NO: 14, 17 or 21.

13. The CAR according to claim 1, comprising an amino acid sequence comprising any one of SEQ ID NOs: 22-24.

14. The CAR according to claim 1, wherein the intracellular T cell signaling domain comprises an intracellular signaling portion of a CD28 or comprises an intracellular signaling portion of a CD137 and wherein the CAR does not comprise an intracellular signaling portion of both a CD28 and a CD137.

15. The CAR according to claim 14, wherein the CAR does not comprise an intracellular signaling domain of more than one T cell costimulatory molecule.

16. The CAR of claim 1, comprising and amino acid sequence comprising SEQ ID NO: 22.

17. The CAR of claim 1, comprising and amino acid sequence comprising SEQ ID NO: 23.

18. The CAR of claim 1, comprising and amino acid sequence comprising SEQ ID NO: 24.

* * * * *

UNITED STATES PATENT AND TRADEMARK OFFICE
CERTIFICATE OF CORRECTION

PATENT NO. : 10,072,078 B2
APPLICATION NO. : 14/437889
DATED : September 11, 2018
INVENTOR(S) : Rimas J. Orentas et al.

Page 1 of 1

It is certified that error appears in the above-identified patent and that said Letters Patent is hereby corrected as shown below:

In the Claims

Column 54, In Claim 16, Line 12, please delete "and" and add --an--

Column 54, In Claim 17, Line 14, please delete "and" and add --an--

Column 54, In Claim 18, Line 16, please delete "and" and add --an--

Signed and Sealed this
Thirtieth Day of January, 2024

Katherine Kelly Vidal
*Director of the United States Patent and Trademark Office*

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Asp Ser Val Ser Ser Asn Ser Ala Ala
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Thr Tyr Tyr Arg Ser Lys Trp Tyr Asn
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Ala Arg Glu Val Thr Gly Asp Leu Glu Asp Ala Phe Asp Ile
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gln Thr Ile Trp Ser Tyr
1               5

<210> SEQ ID NO 5
<211> LENGTH: 3
<212> TYPE: PRT
<213> ORGANISM: Artificial Sequence
```

```
<220> FEATURE:
<223> OTHER INFORMATION: Synthetic

<400> SEQUENCE: 5

Ala Ala Ser
1

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gln Gln Ser Tyr Ser Ile Pro Gln Thr Phe
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Synthetic

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Trp Ser Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Ala
65                  70                  75                  80

Glu Asp Phe Ala Thr Tyr Tyr Cys Gln Gln Ser Tyr Ser Ile Pro Gln
                85                  90                  95

Thr Phe Gly Gln Gly Thr Lys Leu Glu Ile Lys
            100                 105

<210> SEQ ID NO 8
<211> LENGTH: 124
<212> TYPE: PRT
<213> ORGANISM: Artificial Sequence
<220> FEATURE:
<223> OTHER INFORMATION: Synthetic

<400> SEQUENCE: 8

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 9
<211> LENGTH: 236
<212> TYPE: PRT
<213> ORGANISM: Artificial Sequence
<220> FEATURE:
<223> OTHER INFORMATION: Synthetic

<400> SEQUENCE: 9

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Asp Ile Gln Met Thr Gln Ser Pro Ser Ser Leu Ser Ala Ser Val
    130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
            180                 185                 190

Gly Arg Gly Ser Gly Thr Asp Phe Thr Leu Thr Ile Ser Ser Leu Gln
        195                 200                 205

Ala Glu Asp Phe Ala Thr Tyr Tyr Cys Gln Gln Ser Tyr Ser Ile Pro
    210                 215                 220

Gln Thr Phe Gly Gln Gly Thr Lys Leu Glu Ile Lys
225                 230                 235

<210> SEQ ID NO 10
<211> LENGTH: 22
<212> TYPE: PRT
<213> ORGANISM: Artificial Sequence
<220> FEATURE:
<223> OTHER INFORMATION: Synthetic

<400> SEQUENCE: 10

Met Leu Leu Leu Val Thr Ser Leu Leu Leu Cys Glu Leu Pro His Pro
1               5                   10                  15

Ala Phe Leu Leu Ile Pro
            20

```
<210> SEQ ID NO 11
<211> LENGTH: 5
<212> TYPE: PRT
<213> ORGANISM: Artificial Sequence
<220> FEATURE:
<223> OTHER INFORMATION: Synthetic

<400> SEQUENCE: 11

Gly Gly Gly Gly Ser
1               5

<210> SEQ ID NO 12
<211> LENGTH: 69
<212> TYPE: PRT
<213> ORGANISM: Artificial Sequence
<220> FEATURE:
<223> OTHER INFORMATION: Synthetic

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 13
<211> LENGTH: 42
<212> TYPE: PRT
<213> ORGANISM: Artificial Sequence
<220> FEATURE:
<223> OTHER INFORMATION: Synthetic

<400> SEQUENCE: 13

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 14
<211> LENGTH: 112
<212> TYPE: PRT
<213> ORGANISM: Artificial Sequence
<220> FEATURE:
<223> OTHER INFORMATION: Synthetic

<400> SEQUENCE: 14

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
```

```
                65                  70                  75                  80
Arg Arg Gly Lys Gly His Asp Gly Leu Tyr Gln Gly Leu Ser Thr Ala
                    85                  90                  95

Thr Lys Asp Thr Tyr Asp Ala Leu His Met Gln Ala Leu Pro Pro Arg
                    100                 105                 110

<210> SEQ ID NO 15
<211> LENGTH: 65
<212> TYPE: PRT
<213> ORGANISM: Artificial Sequence
<220> FEATURE:
<223> OTHER INFORMATION: Synthetic

<400> SEQUENCE: 15

Val Met Tyr Pro Pro Tyr Leu Asp Asn Glu Lys Ser Asn Gly Thr
1               5                   10                  15

Ile Ile His Val Lys Gly Lys His Leu Cys Pro Ser Pro Leu Phe Pro
                20                  25                  30

Gly Pro Ser Lys Pro Phe Trp Val Leu Val Val Gly Gly Val Leu
                35                  40                  45

Ala Cys Tyr Ser Leu Leu Val Thr Val Ala Phe Ile Ile Phe Trp Val
            50                  55                  60

Arg
65

<210> SEQ ID NO 16
<211> LENGTH: 40
<212> TYPE: PRT
<213> ORGANISM: Artificial Sequence
<220> FEATURE:
<223> OTHER INFORMATION: Synthetic

<400> SEQUENCE: 16

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
                20                  25                  30

Arg Asp Phe Ala Ala Tyr Arg Ser
            35                  40

<210> SEQ ID NO 17
<211> LENGTH: 112
<212> TYPE: PRT
<213> ORGANISM: Artificial Sequence
<220> FEATURE:
<223> OTHER INFORMATION: Synthetic

<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                    85                  90                  95
```

```
Thr Lys Asp Thr Tyr Asp Ala Leu His Met Gln Ala Leu Pro Pro Arg
            100                 105                 110
```

<210> SEQ ID NO 18
<211> LENGTH: 84
<212> TYPE: PRT
<213> ORGANISM: Artificial Sequence
<220> FEATURE:
<223> OTHER INFORMATION: Synthetic

<400> SEQUENCE: 18

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 19
<211> LENGTH: 40
<212> TYPE: PRT
<213> ORGANISM: Artificial Sequence
<220> FEATURE:
<223> OTHER INFORMATION: Synthetic

<400> SEQUENCE: 19

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

<210> SEQ ID NO 20
<211> LENGTH: 47
<212> TYPE: PRT
<213> ORGANISM: Artificial Sequence
<220> FEATURE:
<223> OTHER INFORMATION: Synthetic

<400> SEQUENCE: 20

```
Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Gly Gly Cys Glu Leu
        35                  40                  45
```

<210> SEQ ID NO 21
<211> LENGTH: 112
<212> TYPE: PRT
<213> ORGANISM: Artificial Sequence
<220> FEATURE:
<223> OTHER INFORMATION: Synthetic

<400> SEQUENCE: 21

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 22
<211> LENGTH: 484
<212> TYPE: PRT
<213> ORGANISM: Artificial Sequence
<220> FEATURE:
<223> OTHER INFORMATION: Synthetic

<400> SEQUENCE: 22

```
Met Leu Leu Leu Val Thr Ser Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
            115                 120                 125

Leu Glu Asp Ala Phe Asp Ile Trp Gly Gln Gly Thr Met Val Thr Val
130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
        195                 200                 205

Val Pro Ser Arg Phe Ser Gly Arg Gly Ser Gly Thr Asp Phe Thr Leu
210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255
```

```
Ile Lys Ala Ala Ala Thr Thr Thr Pro Ala Pro Arg Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
            325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
            355                 360                 365

Gly Cys Glu Leu Arg Val Lys Phe Ser Arg Ser Ala Asp Ala Pro Ala
    370                 375                 380

Tyr Lys Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 23
<211> LENGTH: 480
<212> TYPE: PRT
<213> ORGANISM: Artificial Sequence
<220> FEATURE:
<223> OTHER INFORMATION: Synthetic

<400> SEQUENCE: 23

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
```

```
            130                 135                 140
Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
                195                 200                 205

Val Pro Ser Arg Phe Ser Gly Arg Gly Ser Gly Thr Asp Phe Thr Leu
            210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Ala Ala Ala Ile Glu Val Met Tyr Pro Pro Pro Tyr Leu Asp
                260                 265                 270

Asn Glu Lys Ser Asn Gly Thr Ile Ile His Val Lys Gly Lys His Leu
            275                 280                 285

Cys Pro Ser Pro Leu Phe Pro Gly Pro Ser Lys Pro Phe Trp Val Leu
            290                 295                 300

Val Val Val Gly Gly Val Leu Ala Cys Tyr Ser Leu Leu Val Thr Val
305                 310                 315                 320

Ala Phe Ile Ile Phe Trp Val Arg Ser Lys Arg Ser Arg Leu Leu His
                325                 330                 335

Ser Asp Tyr Met Asn Met Thr Pro Arg Arg Pro Gly Pro Thr Arg Lys
            340                 345                 350

His Tyr Gln Pro Tyr Ala Pro Pro Arg Asp Phe Ala Ala Tyr Arg Ser
            355                 360                 365

Arg Val Lys Phe Ser Arg Ser Ala Asp Ala Pro Ala Tyr Gln Gln Gly
            370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
            435                 440                 445

Arg Arg Gly Lys Gly His Asp Gly Leu Tyr Gln Gly Leu Ser Thr Ala
            450                 455                 460

Thr Lys Asp Thr Tyr Asp Ala Leu His Met Gln Ala Leu Pro Pro Arg
465                 470                 475                 480

<210> SEQ ID NO 24
<211> LENGTH: 544
<212> TYPE: PRT
<213> ORGANISM: Artificial Sequence
<220> FEATURE:
<223> OTHER INFORMATION: Synthetic

<400> SEQUENCE: 24

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
```

```
                    20                  25                  30
Leu Val Lys Pro Ser Gln Thr Leu Ser Leu Thr Cys Ala Ile Ser Gly
                35                  40                  45

Asp Ser Val Ser Ser Asn Ser Ala Ala Trp Asn Trp Ile Arg Gln Ser
            50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
            115                 120                 125

Leu Glu Asp Ala Phe Asp Ile Trp Gly Gln Gly Thr Met Val Thr Val
            130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
            195                 200                 205

Val Pro Ser Arg Phe Ser Gly Arg Gly Ser Gly Thr Asp Phe Thr Leu
            210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Ala Ala Ala Phe Val Pro Val Phe Leu Pro Ala Lys Pro Thr
            260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
            290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Arg Asn Arg Ser Lys Arg Ser Arg Leu Leu
            340                 345                 350

His Ser Asp Tyr Met Asn Met Thr Pro Arg Arg Pro Gly Pro Thr Arg
            355                 360                 365

Lys His Tyr Gln Pro Tyr Ala Pro Pro Arg Asp Phe Ala Ala Tyr Arg
            370                 375                 380

Ser Arg Phe Ser Val Val Lys Arg Gly Arg Lys Lys Leu Leu Tyr Ile
385                 390                 395                 400

Phe Lys Gln Pro Phe Met Arg Pro Val Gln Thr Thr Gln Glu Glu Asp
                405                 410                 415

Gly Cys Ser Cys Arg Phe Pro Glu Glu Glu Glu Gly Gly Cys Glu Leu
            420                 425                 430

Arg Val Lys Phe Ser Arg Ser Ala Asp Ala Pro Ala Tyr Gln Gln Gly
            435                 440                 445
```

```
Gln Asn Gln Leu Tyr Asn Glu Leu Asn Leu Gly Arg Arg Glu Glu Tyr
    450                 455                 460
Asp Val Leu Asp Lys Arg Arg Gly Arg Asp Pro Glu Met Gly Gly Lys
465                 470                 475                 480
Pro Arg Arg Lys Asn Pro Gln Glu Gly Leu Tyr Asn Glu Leu Gln Lys
                485                 490                 495
Asp Lys Met Ala Glu Ala Tyr Ser Glu Ile Gly Met Lys Gly Glu Arg
            500                 505                 510
Arg Arg Gly Lys Gly His Asp Gly Leu Tyr Gln Gly Leu Ser Thr Ala
        515                 520                 525
Thr Lys Asp Thr Tyr Asp Ala Leu His Met Gln Ala Leu Pro Pro Arg
    530                 535                 540

<210> SEQ ID NO 25
<211> LENGTH: 774
<212> TYPE: DNA
<213> ORGANISM: Artificial Sequence
<220> FEATURE:
<223> OTHER INFORMATION: Synthetic

<400> SEQUENCE: 25
atgcttctgc tcgtgacaag cctgctgctg tgcgagctgc cccaccctgc ctttctgctg     60
atccctcagg tgcagctgca gcagtctggc cctggcctcg tgaagcctag ccagaccctg    120
agcctgacct gtgccatcag cggcgatagc gtgtccagca atagcgccgc tggaactgg    180 atcagacaga gccctagcag aggcctggaa tggctgggcc ggacctacta ccggtccaag    240
tggtacaacg actacgccgt gtccgtgaag tcccggatca ccatcaaccc cgacaccagc    300
aagaaccagt tctccctgca gctgaacagc gtgacccccg aggataccgc cgtgtactac    360
tgcgccagag aagtgaccgg cgacctggaa gatgccttcg acatctgggg ccagggcaca    420
atggtcaccg tgtctagcgg aggcggcgga agcgacatcc agatgacaca gagccccagc    480
tccctgagcg ccagcgtggg agacagagtg accatcacct gtcgggccag ccagaccatc    540
tggtcctacc tgaactggta tcagcagcgg cctggcaagg ccccaacct gctgatctat    600 gccgccagct cactgcagag cggcgtgccc agcagatttt ccggcagagg cagcggcacc    660
gacttcaccc tgacaatcag ttccctgcag ccgaggact cgccaccta ctactgccag    720 cagagctaca gcatccccca gaccttcggc caggggacca agctggaaat caaa         774

<210> SEQ ID NO 26
<211> LENGTH: 672
<212> TYPE: DNA
<213> ORGANISM: Artificial Sequence
<220> FEATURE:
<223> OTHER INFORMATION: Synthetic

<400> SEQUENCE: 26
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgatatcta catctgggcg cccttggccg ggacttgtgg ggtccttctc    180
ctgtcactgg ttatcaccct ttactgcaaa cggggcagaa agaaactcct gtatatattc    240
aaacaaccat ttatgagacc agtacaaact actcaagagg aagatggctg tagctgccga    300
tttccagaag aagaagaagg aggatgtgaa ctgagagtga agttcagcag gagcgcagac    360 gccccgcgt acaagcaggg ccagaaccag ctctataacg agctcaatct aggacgaaga    420
```

| | |
|---|---|
| gaggagtacg atgttttgga caagagacgt ggccgggacc ctgagatggg gggaaagccg | 480 |
| agaaggaaga accctcagga aggcctgtac aatgaactgc agaaagataa gatggcggag | 540 |
| gcctacagtg agattgggat gaaaggcgag cgccggaggg gcaaggggca cgatggcctt | 600 |
| taccagggtc tcagtacagc caccaaggac acctacgacg cccttcacat gcaggccctg | 660 |
| cccctcgct aa | 672 |

<210> SEQ ID NO 27
<211> LENGTH: 654
<212> TYPE: DNA
<213> ORGANISM: Artificial Sequence
<220> FEATURE:
<223> OTHER INFORMATION: Synthetic

<400> SEQUENCE: 27

| | |
|---|---|
| gttatgtatc ctcctcctta cctagacaat gagaagagca atggaaccat tatccatgtg | 60 |
| aaagggaaac acctttgtcc aagtccccta tttcccggac cttctaagcc cttttgggtg | 120 |
| ctggtggtgg ttggtggagt cctggcttgc tatagcttgc tagtaacagt ggcctttatt | 180 |
| attttctggg tgaggagtaa gaggagcagg ctcctgcaca gtgactacat gaacatgact | 240 |
| ccccgccgcc ccgggcccac ccgcaagcat taccagccct atgccccacc acgcgacttc | 300 |
| gcagcctatc gctccagagt gaagttcagc aggagcgcag acgccccgc gtaccagcag | 360 |
| ggccagaacc agctctataa cgagctcaat ctaggacgaa gagaggagta cgatgttttg | 420 |
| gacaagagac gtggccggga ccctgagatg ggggaaagc cgagaaggaa gaaccctcag | 480 |
| gaaggcctgt acaatgaact gcagaaagat aagatggcgg aggcctacag tgagattggg | 540 |
| atgaaaggcg agcgccggag gggcaagggg cacgatggcc tttaccaggg tctcagtaca | 600 |
| gccaccaagg acacctacga cgcccttcac atgcaggccc tgccccctcg ctaa | 654 |

<210> SEQ ID NO 28
<211> LENGTH: 852
<212> TYPE: DNA
<213> ORGANISM: Artificial Sequence
<220> FEATURE:
<223> OTHER INFORMATION: Synthetic

<400> SEQUENCE: 28

| | |
|---|---|
| ttcgtgccgg tcttcctgcc agcgaagccc accacgacgc cagcgccgcg accaccaaca | 60 |
| ccggcgccca ccatcgcgtc gcagcccctg tccctgcgcc cagaggcgtg ccggccagcg | 120 |
| gcgggggggcg cagtgcacac gagggggctg gacttcgcct gtgatatcta catctgggcg | 180 |
| cccttggccg ggacttgtgg ggtccttctc ctgtcactgg ttatcaccct ttactgcaac | 240 |
| cacaggaaca ggagtaagag gagcaggctc ctgcacagtg actacatgaa catgactccc | 300 |
| cgccgccccg ggcccacccg caagcattac cagccctatg ccccaccacg cgacttcgca | 360 |
| gcctatcgct cccgtttctc tgttgttaaa cggggcagaa agaagctcct gtatatattc | 420 |
| aaacaaccat ttatgagacc agtacaaact actcaagagg aagatggctg tagctgccga | 480 |
| tttccagaag aagaagaagg aggatgtgaa ctgagagtga agttcagcag gagcgcagac | 540 |
| gccccgcgt accagcaggg ccagaaccag ctctataacg agctcaatct aggacgaaga | 600 |
| gaggagtacg atgttttgga caagagacgt ggccgggacc ctgagatggg gggaaagccg | 660 |
| agaaggaaga accctcagga aggcctgtac aatgaactgc agaaagataa gatggcggag | 720 |
| gcctacagtg agattgggat gaaaggcgag cgccggaggg gcaaggggca cgatggcctt | 780 |
| taccagggtc tcagtacagc caccaaggac acctacgacg cccttcacat gcaggccctg | 840 |

```
ccccctcgct aa                                                                852

<210> SEQ ID NO 29
<211> LENGTH: 6
<212> TYPE: DNA
<213> ORGANISM: Artificial Sequence
<220> FEATURE:
<223> OTHER INFORMATION: Synthetic

<400> SEQUENCE: 29 ctcgag                                                                         6

<210> SEQ ID NO 30
<211> LENGTH: 8
<212> TYPE: DNA
<213> ORGANISM: Artificial Sequence
<220> FEATURE:
<223> OTHER INFORMATION: Synthetic

<400> SEQUENCE: 30 gcggccgc                                                                       8

<210> SEQ ID NO 31
<211> LENGTH: 6
<212> TYPE: DNA
<213> ORGANISM: Artificial Sequence
<220> FEATURE:
<223> OTHER INFORMATION: Synthetic

<400> SEQUENCE: 31 ggatcc                                                                         6

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
taaggatccg ataaaataa                                                          19

<210> SEQ ID NO 33
<211> LENGTH: 15
<212> TYPE: DNA
<213> ORGANISM: Artificial Sequence
<220> FEATURE:
<223> OTHER INFORMATION: Synthetic

<400> SEQUENCE: 33
ctaaggatcc gataa                                                              15
```